(12) United States Patent
Johnson et al.

(10) Patent No.: US 10,117,462 B2
(45) Date of Patent: Nov. 6, 2018

(54) PERSONAL ELECTRONIC VAPORIZER

(71) Applicant: Intrepid Brands, LLC, Louisville, KY (US)

(72) Inventors: David M. Johnson, Owensboro, KY (US); Charles H. Melander, Owensboro, KY (US); Michael G. Terry, Prospect, KY (US); Curtis R. Berry, Louisville, KY (US); Trent Edward Grantz, Crestwood, KY (US)

(73) Assignee: Intrepid Brands, LLC, Louisville, KY (US)

( * ) Notice: Subject to any disclaimer, the term of this patent is extended or adjusted under 35 U.S.C. 154(b) by 72 days.

(21) Appl. No.: 15/013,500

(22) Filed: Feb. 2, 2016

(65) Prior Publication Data

US 2016/0227838 A1   Aug. 11, 2016

Related U.S. Application Data

(60) Provisional application No. 62/110,838, filed on Feb. 2, 2015.

(51) Int. Cl.
*A24F 47/00* (2006.01)
*A61M 15/06* (2006.01)
(Continued)

(52) U.S. Cl.
CPC ......... *A24F 47/008* (2013.01); *A61M 11/042* (2014.02); *A61M 15/002* (2014.02);
(Continued)

(58) Field of Classification Search
CPC ................................................... A24F 47/008
See application file for complete search history.

(56) References Cited

U.S. PATENT DOCUMENTS 5,086,766 A * 2/1992 Beacham ............... A61M 16/16
128/203.17
5,564,442 A * 10/1996 MacDonald .......... A24F 47/008
131/194
(Continued)

FOREIGN PATENT DOCUMENTS

WO   WO 2013/138384 A2   9/2013

OTHER PUBLICATIONS

"Billy Wu's Review—Volcano Vaporizer." The AutoFlower Network—AFN, WayBack Machine Generated NPL, Nov. 14, 2012, www.autoflower.net/forums/threads/billy-wus-review-volcano-vaporizer.13736/.*

(Continued)

*Primary Examiner* — Seyed Masoud Malekzadeh
*Assistant Examiner* — Taryn Trace Willett
(74) *Attorney, Agent, or Firm* — Frost Brown Todd LLC

(57) ABSTRACT

The disclosure relates to a personal electronic vaporizer configured to receive a selected oven assembly and heat the medium therein in accordance with a heating profile associate with the selected oven assembly. The personal electronic vaporizer may define a pathway entirely surrounded by a material. The material is preferably an inert material such as glass or a material otherwise desirable to channel the vapors emitted by the heated medium to the user. The user may swap or select a different oven assembly associated with a different heating profile. The first oven assembly is thereafter removed from the personal electronic vaporizer and replaced with the newly selected oven assembly. The personal electronic vaporizer may automatically recognize the particular selected oven assembly and heat the substance therein according to a predefined heating profile associate with the oven assembly.

20 Claims, 14 Drawing Sheets

(51) Int. Cl.

| | | |
|---|---|---|
| *A61M 11/04* | (2006.01) | |
| *A61M 15/00* | (2006.01) | |
| *H04R 1/02* | (2006.01) | |
| *H05B 1/02* | (2006.01) | |
| *H05B 3/00* | (2006.01) | |
| *A61M 21/00* | (2006.01) | |

(52) U.S. Cl.
CPC ........ *A61M 15/0021* (2014.02); *A61M 15/06* (2013.01); *H04R 1/028* (2013.01); *H05B 1/0202* (2013.01); *H05B 3/0014* (2013.01); *A61M 2021/0027* (2013.01); *A61M 2205/02* (2013.01); *A61M 2205/127* (2013.01); *A61M 2205/3368* (2013.01); *A61M 2205/3569* (2013.01); *A61M 2205/3592* (2013.01); *A61M 2205/3653* (2013.01); *A61M 2205/502* (2013.01); *A61M 2205/581* (2013.01); *A61M 2205/6018* (2013.01); *A61M 2205/6054* (2013.01); *A61M 2205/75* (2013.01); *A61M 2205/8206* (2013.01); *A61M 2205/8237* (2013.01)

(56) References Cited

U.S. PATENT DOCUMENTS

| | | | | |
|---|---|---|---|---|
| 6,250,301 | B1 * | 6/2001 | Pate | A61M 11/041 128/202.21 |
| 6,513,524 | B1 * | 2/2003 | Storz | A61M 11/041 128/203.26 |
| 6,603,924 | B2 * | 8/2003 | Brown | A01M 1/2077 219/541 |
| 6,772,756 | B2 * | 8/2004 | Shayan | A61M 11/041 128/202.21 |
| 7,141,215 | B2 * | 11/2006 | Guan | A61L 9/03 239/136 |
| D581,520 | S * | 11/2008 | Williams | D23/360 |
| 7,537,009 | B2 * | 5/2009 | Hale | A61K 9/007 128/200.14 |
| 7,589,340 | B2 * | 9/2009 | Dancs | A01M 1/2077 250/577 |
| 9,149,586 | B2 * | 10/2015 | Shen | A61M 11/041 |
| 9,220,302 | B2 * | 12/2015 | DePiano | A24F 47/008 |
| 9,237,770 | B2 * | 1/2016 | Bavar | A24F 1/30 |
| 9,399,080 | B2 * | 7/2016 | Irvin | A61L 9/03 |
| 9,609,893 | B2 * | 4/2017 | Novak, III | A24F 47/008 |
| 2007/0068523 | A1 * | 3/2007 | Fishman | A61M 16/0051 128/203.12 |
| 2012/0097660 | A1 * | 4/2012 | Bao | A61M 11/041 219/209 |
| 2013/0152922 | A1 | 6/2013 | Benassayag et al. | |
| 2014/0123989 | A1 | 5/2014 | LaMothe | |
| 2014/0314397 | A1 * | 10/2014 | Alima | A24F 47/008 392/386 |
| 2014/0338686 | A1 * | 11/2014 | Plojoux | A24F 47/008 131/329 |
| 2014/0353856 | A1 * | 12/2014 | Dubief | A24D 3/041 261/128 |
| 2014/0373857 | A1 * | 12/2014 | Steinberg | A24F 47/008 131/329 |
| 2015/0114409 | A1 * | 4/2015 | Brammer | H05B 3/02 131/329 |
| 2015/0128976 | A1 * | 5/2015 | Verleur | A24F 47/008 131/329 |
| 2016/0249677 | A1 * | 9/2016 | Bishara | A24F 1/30 131/329 |
| 2016/0302486 | A1 * | 10/2016 | Eroch | A24F 47/008 |
| 2017/0055574 | A1 * | 3/2017 | Kaufman | A24F 47/004 |

OTHER PUBLICATIONS

"Top Quartz Ceramic Cotton Replacement Atomizer Dual Glass Globe Coils Donut Wax Dry Herb Herbal Vaporizers Vape Pen E Cigarettes Vapor Core Dry Herb Coils Quartz Coils Glass Tank Core Online with $0.68/Piece on Chinabuyecigs's Store." Op Quartz Ceramic Cotton Replacement Atomizer, DH Gate, Sep. 8, 2013, www.dhgate.com/store/product/glass-tank-coil.*

"Types of Percolator Bongs." BestBongReviews.com, Wayback Machine Generated NPL, Sep. 24, 2014, bestbongreviews.com:80/types-percolator-bongs/.*

"V2 Pro Series 3 Vaporizer Review." Vapegrl.com, Wayback Machine Cited NPL, Jul. 21, 2014, vapegrl.com:80/v2-pro-series-3-vaporizer-review/.*

VaporizerWizard. "V2 Pro Series 3 Vaporizer Review w/ Loose-Leaf Demo." Vaporizer Wizard, Wayback Machine Generated NPL, Nov. 4, 2014, www.vaporizerwizard.com:80/v2-pro-series-3-vaporizer-review/.*

International Search Report and Written Opinion dated May 3, 2016 for Application No. PCT/US2016/016155, 15 pgs.

* cited by examiner

PERSONAL ELECTRONIC VAPORIZER

PRIORITY

This application claims priority to U.S. Provisional Patent Application Ser. No. 62/110,838, filed Feb. 2, 2015, entitled "Personal Electronic Vaporizer," the disclosure of which is incorporated by reference herein.

TECHNICAL FIELD

The present disclosure is directed to personal electronic vaporizers, which may be used to generate vapor from a number of substances, such as by using interchangeable heating chambers or oven assemblies comprising unexposed heating elements.

BACKGROUND

Smoking devices, such as cigarette holders and pipes, are well known in the art for providing flavored vapor from a smokable substance to a user for therapeutic or smoking pleasure. However, such devices provide no means of controlling the heating and combustion of tobacco and other products. As a result, the devices tend to produce by-products which may impart a bitter and/or burnt taste to the mouth of a user.

In an effort to overcome these issues, there have been numerous attempts to provide a device for delivering an active ingredient to a consumer through vaporization rather than combustion. For instance, many of the personal electronic vaporizers that are currently on the market heat a substance without burning it in order to release a vapor that contains the active ingredient(s) to be delivered to the user. In some instances, the vapor is created by placing the substance in contact with a metallic heating coil inside of a chamber, which may also be made of metal. Airflow is directed past the heated substance and exposed coil, often through pathways constructed of metal, resulting in the desired delivery of the vapor to the user. However, contact with metal may impart the vapor with undesirable flavor.

In addition to eliminating issues with the taste of vapor, most personal electronic vaporizers do not provide means for customizing the vaping experience. For example, many personal electronic vaporizers utilize the same heating profiles regardless of type of substance to be vaporized, e.g. a solid, liquid or wax. As a result, the user may not have the option to heat the substance to an ideal temperature that will maximize vapor generation without combusting the substance. Moreover, many personal electronic vaporizers fail to provide the user with an integrated means of filtering the vapor, and/or adjusting the flow of vapor to the user in a desired amount. For these and other reasons, there remains a need for a personal electronic vaporizer that allows for the delivery of a good tasting vapor to a user, while providing the user with a customizable vaping experience. While a variety of personal electronic vaporizers have been made and used, it is believed that no one prior to the inventors has made or used an invention as described herein.

SUMMARY

The personal electronic vaporizer (hereinafter "PEV") according to the present disclosure provides a number of advantages over the vaporizers that are currently on the market. For example, the PEV may be constructed so that the substance to be heated does not come into contact with any metallic surfaces. This may be achieved by encasing or enclosing the metal heating coil in glass mod/or a glass coated substance. Moreover, the airflow pathways mod/or heating chamber of the PEV may also be constructed of glass and/or glass coated substances. The REV may also comprise a plurality of ovens or oven assemblies that are interchangeably used to vaporize herbs, waxes and liquids by way of heating profiles that are particularly suited to provide maximum results and which are associated with the particular oven assembly.

In some embodiments of the disclosure, a PEV is described. The PEV may comprise a mouthpiece assembly defining a mouthpiece channel surrounded by a material and including an external portion and an internal portion. The PEV may further comprise a shell assembly extending between a first end and a second end and defining a shell pocket therein. The shell pocket may open through the first end and may be configured to slidably receive the internal portion of the mouthpiece assembly therein. The PEV may further comprise one or more ovens or oven assemblies. For example, the PEV may comprise a first oven assembly including a heating chamber surrounded by the material, and a second oven assembly including a heating chamber surrounded by the material. The PEV may further comprise a battery compartment assembly removably secured to the second end of the shell assembly, and an oven mount assembly removably secured to the battery compartment assembly. The oven mount assembly may be configured to selectively receive one of the first oven assembly and the second oven assembly and align the heating chamber of the selected oven assembly with the mouthpiece channel. The oven mount assembly may be configured to receive the first oven assembly in a first orientation and thereby electronically couple the first oven assembly to the battery in accordance with a first heating profile. The oven mount assembly may also be configured to receive the second oven assembly in a second orientation and thereby electronically couple the second oven assembly to the battery in accordance with a second heating profile.

In some embodiments of the disclosure, a method is described. The method may comprise the following steps: inserting a portion of a mouthpiece assembly into a shell assembly; providing a first oven assembly having a first heating chamber formed of a material, a first connector, and a first identification prong; providing a second oven assembly having a second heating chamber formed of the material, a second connector, and a second identification prong; selecting the first oven assembly; inserting the first oven assembly into an oven mount assembly secured to a battery to electronically couple the first oven assembly with the battery through the first connector; receiving, by the oven mount assembly, the first identification prong; securing the oven mount assembly to the shell assembly; and heating, via the battery, the first heating chamber in accordance with a first heating profile associated with the first identification prong.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawing, in which like reference numerals identify the same elements and in which:

Figure 1:
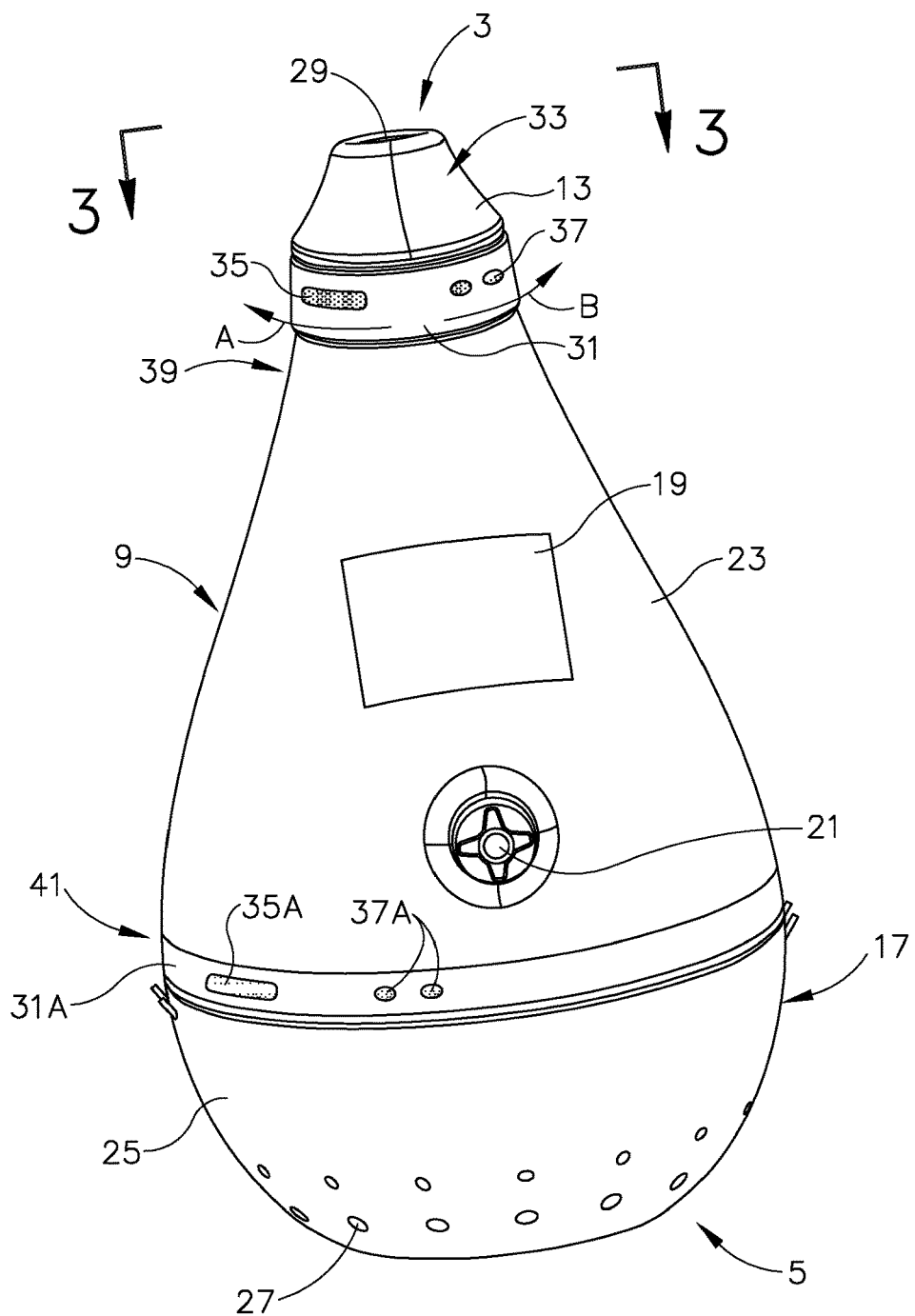
FIG. 1 is a perspective view of an embodiment of a personal electronic vaporizer of the present invention.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

The elements or features of the various embodiments are described in detail hereinafter. Any reference to a singular characteristic or limitation of the present disclosure shall include the corresponding plural characteristics or limitations, and vice versa, unless otherwise specified or clearly implied to the contrary by the context in which the reference is made.

The apparatuses and methods described herein may comprise, consist of or consist essentially of the elements and features of the disclosure described herein, as well as any additional or optional components, or features described herein or otherwise useful in relation to the aforementioned apparatuses and methods.

The term "personal electronic vaporizer," which is used interchangeably herein with "PEV," means a hand held electronic device which vaporizes one or more substances for consumption including, but not limited to, via inhalation, by a consumer. Non-limiting examples of substances include solids, liquids, gels and waxes. The PEV may take any shape to allow for the internal components as described below to be integrated therein.

Figure 2:
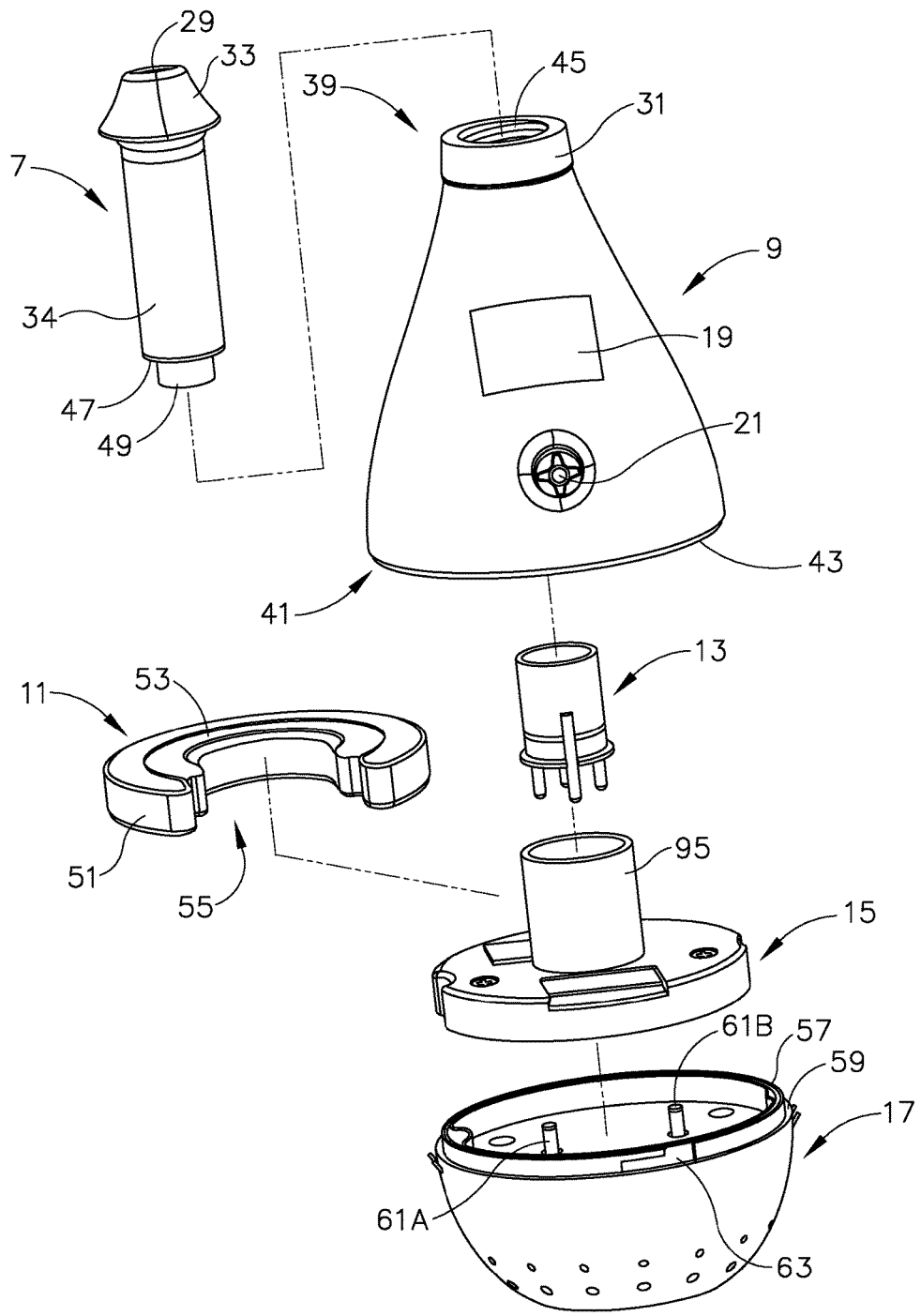
FIG. 2 is an exploded view thereof.
Figure 3:
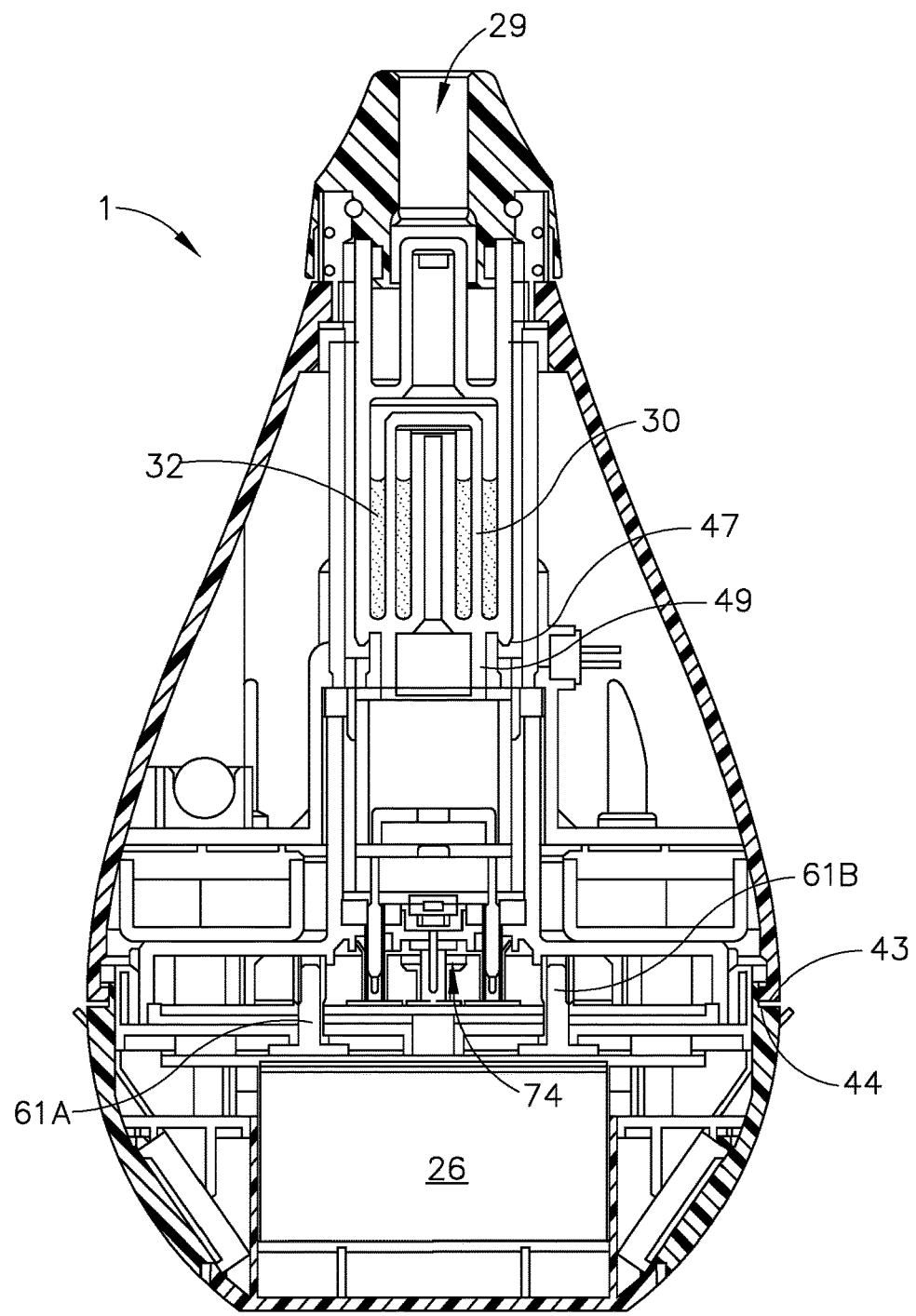
FIG. 3 is a cross-sectional view thereof taken along line 3-3 of FIG. 1.

Referring now to FIGS. 1, 2, and 3, an embodiment of a personal electronic vaporizer is shown and described as PEV 1. PEV 1 extends generally from a top end 3 to a bottom end 5 and includes a mouthpiece assembly 7, a top shell assembly 9, a container assembly 11, one or more of an oven assembly 13, an oven mount assembly 15, and a battery compartment assembly 17. Each component or elements of a component may be formed or coated using a medical grade material, such as medical grade glass or medical grade stainless steel.

Mouthpiece assembly 7 defines a mouthpiece channel 29 surrounded by a material such as glass, ceramics, or polycarbonate. Mouthpiece assembly 7 includes a shaft 34 extending outwardly away from and continuing the channel 29 therethrough. Shaft 34 transitions into a shoulder 47 and a boss 49, with channel 29 extending therethrough. As shown in FIG. 3, channel 29 is a non-linear channel with multiple loop-backs and 180 degree turns as channel 29 extends from mouth area 33 to boss 49 and facilitate fluid communication between mouth area 33 and boss 49. As such, the turning and looping back of channel 29 creates a bubbler area 30 whereby a user may add water or other substances into channel 29 to fill bubbler area 30 and accordingly force any air or fluid passing through PEV 1 to pass through the substance in bubbler area 30. For example, a user may fill bubbler area 30 with an amount of tap water 32. As the user then draws fluid through PEV 1, the fluid passes through the tap water 32 in bubbler area 30 whereby heavier particles and water-soluble molecules are trapped in the tap water 32, thus preventing these particles from entering the user's airways. The user may turn the mouthpiece assembly 7 upside down to empty the tap water 32 from the bubbler area 30.

Top shell assembly 9 extends from a top end 39 to a bottom end 41 and includes a display screen 19 and a button 21. Display screen 19 is configured to be situated behind a mirrored or otherwise one way transparent outer surface 23 of top shell assembly 9, whereby the display screen 19 projects through the outer surface 23 when energized and illuminated, and does not project through the outer surface 23 when the display is not illuminated. Display screen 19 may be a liquid crystal display, a light emitting diode (LED) display, or any other mechanism for displaying visual information. Top shell assembly 9 further includes an annular lip 43 and a corresponding annular shoulder 44 proximate second end 41 for use in securing top shell assembly 9 to battery compartment assembly 17.

Top shell assembly 9 further includes a ring 31 proximate the top end 39. Ring 31 defines a primary intake opening 35 and a secondary intake opening 37 and is rotatable in the direction of Arrow A and Arrow B. Primary intake opening 35 may be rotated with respect to a corresponding underlying opening to adjust the size of the overall fluid pathway leading into the PEV 1. Similarly, secondary air intake opening 37 may be rotated with respect to a corresponding underlying opening to fine tune the size of the overall fluid pathway leading into the PEV 1. By rotating ring 31, the user can adjust the size of the openings for passing fluid into PEV 1 and ultimately affect the flow rate of fluid into the PEV 1. In another embodiment of PEV 1, ring 31 may be embodied by a ring 31A, disposed proximate the second end 41 of top shell assembly 9. Ring 31A operates similarly to ring 31, with a primary intake opening 35A and one or more secondary intake openings 37A. Ring 31A may be manually rotated by the user to open the intake openings in accordance with the preference of the user.

Container assembly 11 includes a hollow body 51 and a corresponding lid 53 for enclosing the hollow body 51. The container assembly 11 is shaped to define a recess 55 which generally corresponds to another portion of the PEV 1 such that the recess 55 mates with the other portion to be snuggly disposed thereon.

Battery compartment assembly 17 includes a battery 26 disposed proximate an outer wall 25. Outer wall 25 defines a series of dimples 27 for aesthetic purposes. Alternatively outer wall 25 may define vent holes (not shown), configured to expel excess heat generated through use of the battery 26 or may utilize vent holes to allow air to enter the PEV 1 and aid in the vaporization. Battery compartment assembly 17 further includes an annular lip 57 and a corresponding annular shoulder 59 sized and oriented to mate with annular lip 43 and annular shoulder 44 of top shell assembly 9 to selectively fittingly engage top shell assembly 9 with battery compartment assembly 17. Battery compartment assembly 17 further includes a pair of electrodes 61 configured to electronically couple with the positive and negative poles of the battery 26. The pair of electrodes 61 are shown in FIGS. 2 and 3 as electrode 61A and electrode 61B. The battery compartment assembly 17 may also include a latch 63 sized and oriented to mate with a corresponding latch (not shown) proximate the second end 41 of the top shell assembly 9 and slidingly engaged therewith to selectively hold top shell assembly 9 to battery compartment assembly 17.

Battery 26 is preferably a rechargeable battery, such as those that are currently used in electronic vaporizers (e.g., nickel cadmium batteries, lithium ion batteries, lithium ion polymer batteries, etc.). The battery may be recharged via an electrical wall outlet, a car charger, and/or a USB on a suitable power source (e.g., a computerized device).

As shown in FIGS. 3-7, oven assembly 13 is sized to be removably received in a heater receptacle 95. As such, oven assembly 13 includes a generally cylindrical profile extending from a top end 67 to a bottom end 69. A pair of electrodes 71 extend outwardly at bottom end 69, with one electrode having a positive pole, shown as electrode 71A, and one electrode having a negative pole, shown as electrode 71B. Electrodes 71 transfer electric power from oven mount assembly 15 to a heating plate 73 configured to heat up and increase in temperature in accordance with the amount of electric power supplied from oven mount assembly 15. Heating plate 73 may include an integrated heating coil (not shown) disposed therein or a thermal film (not shown), a transparent film conductor (not shown), or any other mechanism for converting electrical power from battery 26 into heat.

A preheating area 74 (FIG. 3) may be disposed under and around heating plate 73. Preheating area is configured to be placed in the path of the air traveling through PEV 1 to the oven assembly 13, such as the air is preheated before traveling to oven assembly 13. The preheating area 74 increases the speed with which the PEV 1 may heat the air surrounding the medium in oven assembly 13, which in turn shortens the time the user has to wait to receive the vapors from the properly heated medium in oven assembly 13. The preheating area 74 may be configured to create a convection type of environment, whereby the air is circulated past heating elements to continuously warm and heat the air before the air is drawn into the oven assembly 13.

Figure 5:
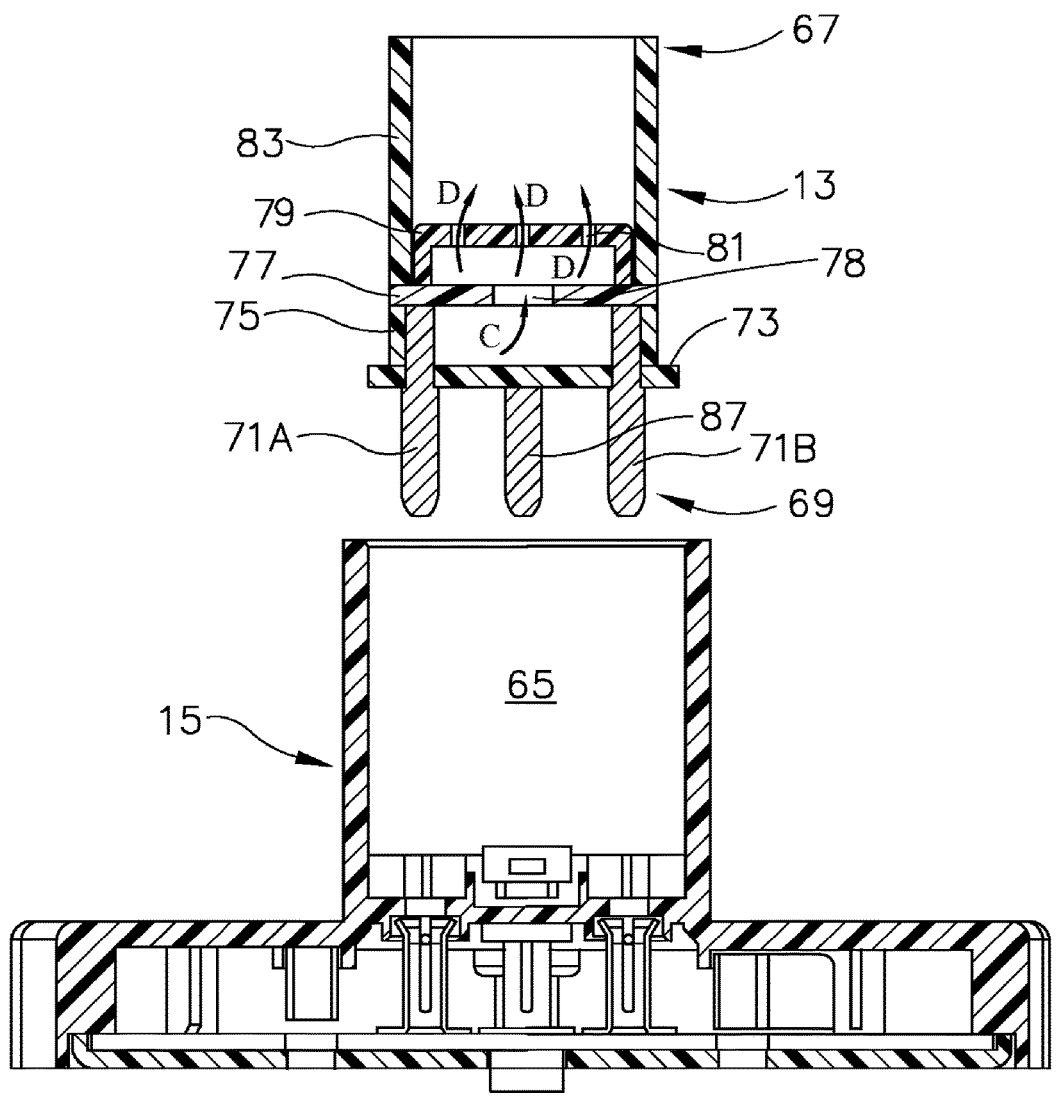
FIG. 5 is a cross-sectional view of the oven assembly and oven mount assembly of FIG. 4.
Figure 6:
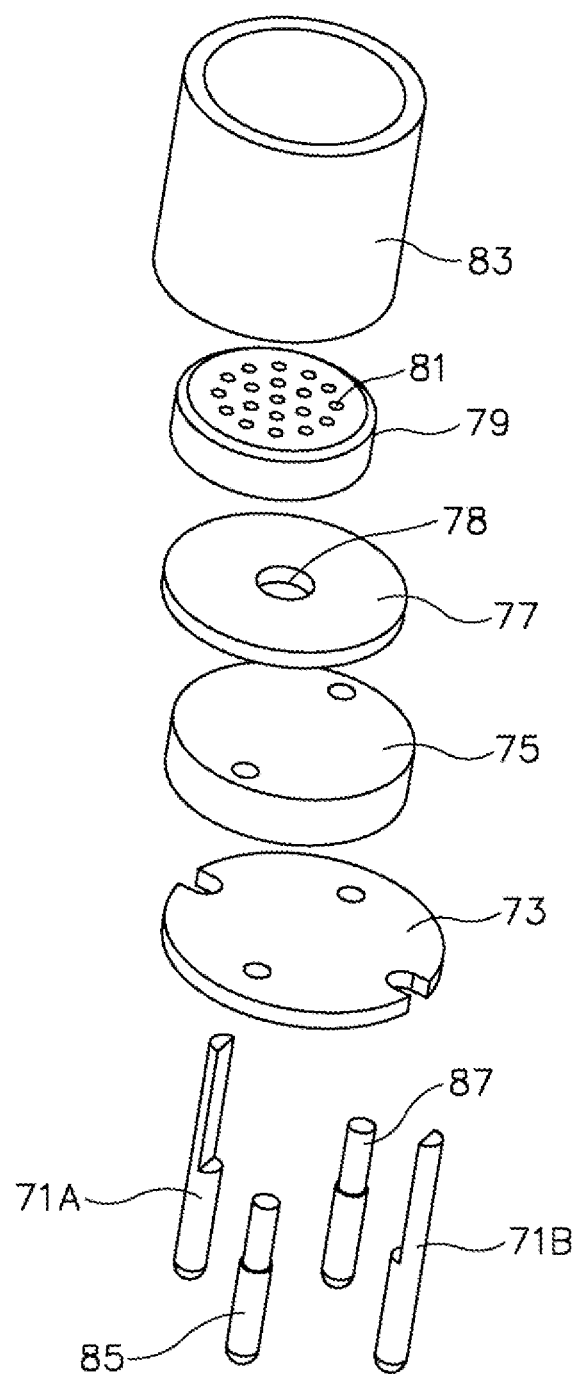
FIG. 6 is an exploded view of the oven assembly of FIG. 4.
Figure 7:
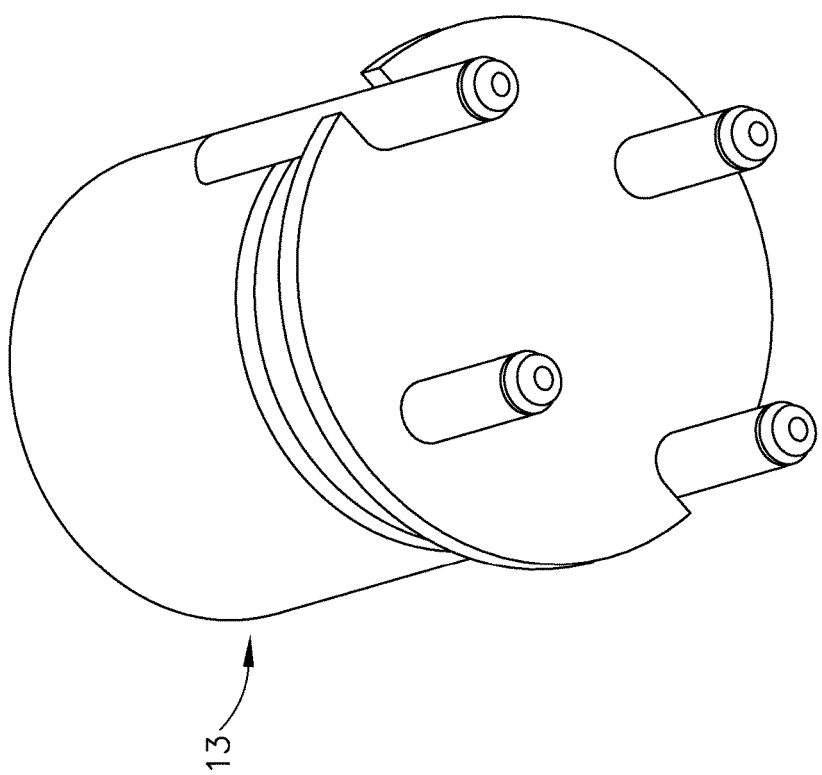
FIG. 7 is a perspective view of the oven assembly of FIG. 4.

As shown in FIGS. 5 and 6 oven assembly 13 further includes a porous ceramic tray 75 in an abutting relationship with heating plate 73 such that ceramic tray 75 absorbs the heat generated by heating plate 73 and changes temperature generally in accordance with heating plate 73. Oven assembly 13 further includes a plenum ring 77 proximate ceramic tray 75 and defining an aperture 78 therethrough. Oven assembly 13 further includes an oven base 79 having a plurality of air holes 81 defined thereby for allowing the air to travel through in the direction of Arrows D. Oven base 79 is topped by a cylindrical shroud 83. As shown in FIG. 5, plenum ring 77 is configured to allow fluid to pass in through aperture 78 in the direction of Arrow C and thereafter pass through air holes 81 of oven base 79 in the direction of Arrows D. Oven assembly 13 may further include a porous glass filter or frit element (not shown) oriented such that the air may travel through the frit relatively slowly, reducing the flow rate of the air as the air travels through a pathway of PEV 1, to allow more time for the air to heat up and retain heat. The frit in turn acts to increase a dwell time for heat transfer along the pathway.

In an embodiment of the invention, the frit or glass filter may be disposed within ceramic tray 75, within aperture 78 and/or air holes 81, or layered between or adjacent to any of the various elements within oven assembly 13. For example, a frit layer may be disposed between plenum ring 77 and oven base 79 to slow the air passing through oven assembly 13 and allow a longer exposure to heating plate 73.

Oven assembly 13 may include zero, one, or two identification prongs. In the illustrated embodiment, oven assembly 13 includes a first identification prong 85 and a second identification prong 87. Identification prongs signal the intended heating profile of the particular oven assembly 13. As will be described in greater detail below, the identified heating profile is used by other components of PEV 1 to heat the oven assembly in accordance with specified criteria. In one embodiment of the present invention, the heating profile includes a goal temperature, wherein the PEV 1 heats the oven assembly 13 to the goal temperature specified by the heating profile. Inasmuch as both the first identification prong 85 and the second identification prong 87 may be present or absent in a particular oven assembly 13, the PEV 1 may use this presence or absence of these two components, or any combination thereof, as a signifier of a particular profile associated with the particular oven assembly 13. For example, the PEV 1 may be configured such that the presence of first identification prong 85 coupled with the absence of the second identification prong 87 indicates to the PEV 1 that a first heating profile is associated with the underlying oven assembly. If the first heating profile includes a goal temperature or goal temperature range of 345 to 355 degrees Fahrenheit, the PEV 1 will act to heat the medium in the oven assembly 13 to between 345 and 355 degrees. The temperature of the medium is determined through one or more sensors configured to sense or derive the temperature of the medium.

As discussed in greater detail below, PEV 1 may include temperature sensors. For example, infrared sensors, thermocouple style sensors, and/or thermistor style sensors for precise temperature sensing of the medium. One major deficiency of in the prior art relates to temperature control. PEV's in the prior art simply measure a mechanical element of the PEV, such as the heating coil or a particular plate or surface, and thereafter base the actuation or termination of the heating on those measured temperatures. However, the temperature of a particular PEV element and the temperature of the underlying medium may vary wildly. Thus, the PEV may actuate or terminate heating in an inefficient manner, with respect to the requirements of the medium for proper and efficient vapor generation. PEV 1 includes multiple sensors and logic circuitry configured to determine or derive the temperature of the medium itself and actuates or terminates the heating based on whether the temperature of the medium is within the goal range. This results in a greater experience for the user through the increased efficiency of heating and vaporizing the medium.

Different smokable substances or mediums may be best suited for different heating profiles. For example, a solid substance may be best suited for a first heating profile, while a liquid substance may be best suited for a second heating profile. Still further, a wax substance may require a third heating profile. As such, the user may select a particular oven assembly 13 based on intended substance and the heating profile associated with the selected oven assembly 13. For example, if a user wishes to vaporize solid tobacco in PEV 1, the user will select the oven assembly 13 configured for use with solid substances and load the selected oven assembly 13 into PEV 1. Thereafter, based on the arrangement of the first identification prong 85 and the second identification prong 87, the PEV 1 will recognize the particular heating profile associated with the selected oven assembly 13 and will heat the oven assembly 13 in the manner best suited for a solid substance.

Correlating the presence or absence of identification prongs is a non-limiting example of a mechanism for signaling different heating profiles in the present invention. Oven assemblies 13 may include alternative mechanisms for signaling a heating profile. For example, in certain configurations of PEV 1, a radio frequency identification (RFID) tags or other similar identification methods may be used or incorporated into the signaling of different heating profiles.

Figure 8:
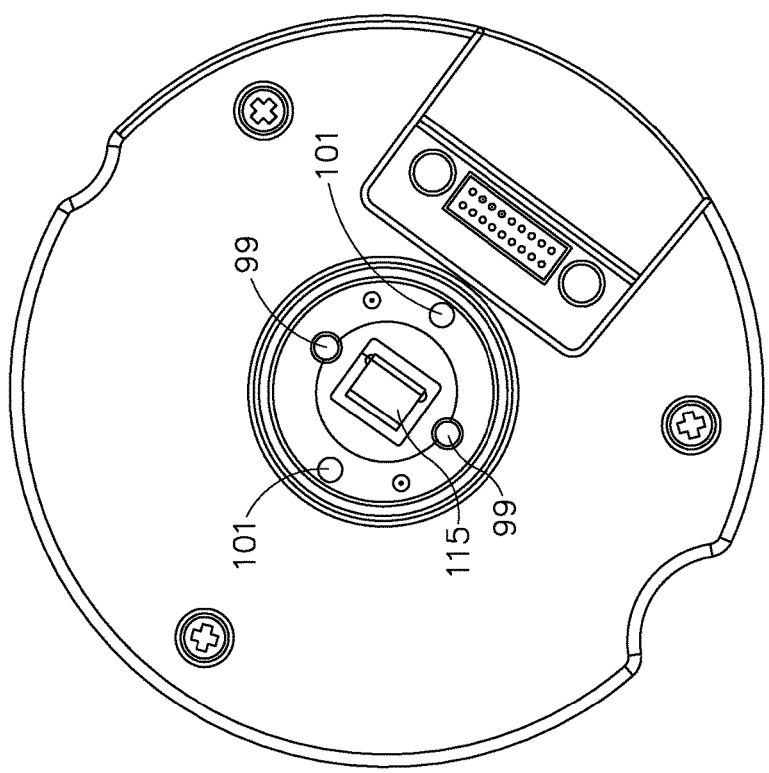
FIG. 8 is a top plan view of the oven mount assembly of FIG. 4.
Figure 9:
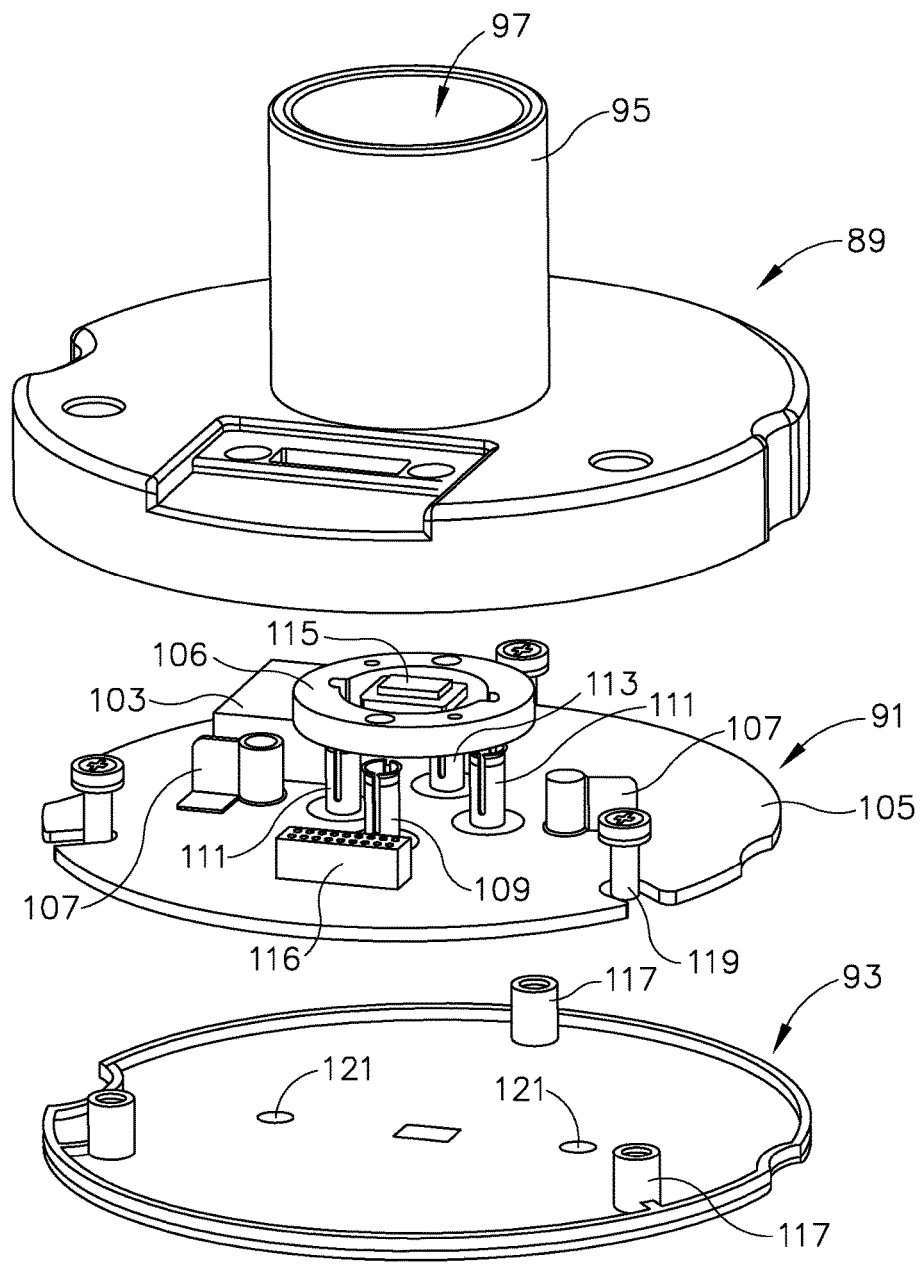
FIG. 9 is an exploded view of the oven mount assembly of FIG. 4.
Figure 10:
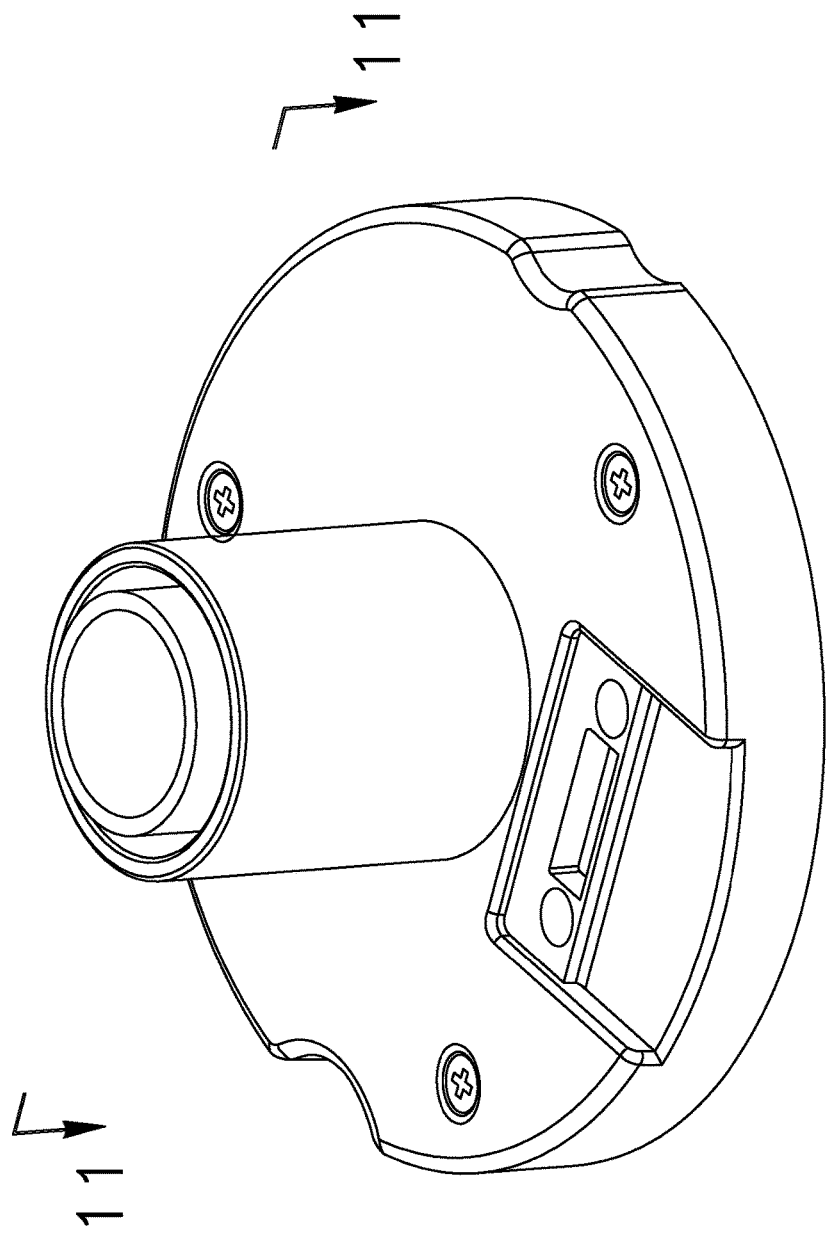
FIG. 10 is a perspective view of the oven assembly of FIG. 4 connected with the oven mount assembly of FIG. 4.
Figure 11:
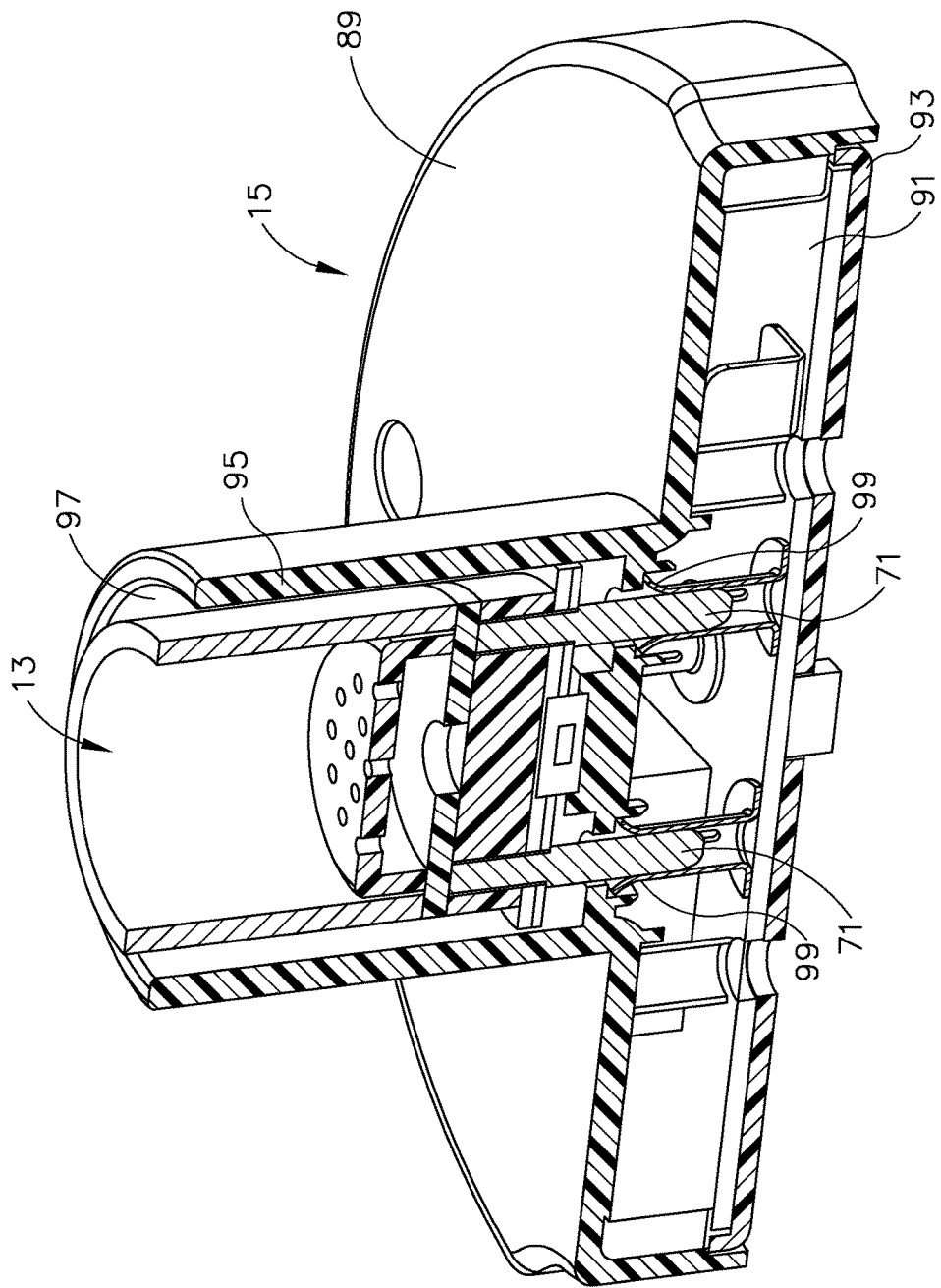
FIG. 11 is a cross-sectional view taken along line 11-11 of FIG. 10.

As shown in FIGS. 5, 8, and 9, oven mount assembly 15 includes three main components: a cap 89, a circuit board assembly 91, and a backing plate 93. Cap 89 defines multiple recesses and apertures for accessing elements on circuit board assembly 91 through cap 89. Cap 89 includes a heater receptacle 95 that defines a channel 97 therein for receiving a selected oven assembly 13. Cap 89 includes a pair of electrode through holes 99 configured to allow a corresponding electrode 71 of an oven assembly 13 to pass through cap 89 and into elements of the circuit board assembly 91 (FIG. 11). Similarly, cap 89 includes a pair of identification prong through holes 101 configured to allow first identification prong 85 and second identification prong 87 to pass through cap 89 and into elements of the circuit board assembly 91. As such, cap 89 is primarily configured to receive a selected oven assembly 13 into heater receptacle 95 and align the electrodes 61 and identification prongs 85 and 87 with underlying elements of circuit board assembly 91.

As shown in FIG. 9, circuit board assembly 91 includes various electronic components, logic, and support structure to enable battery 26 to interface with oven assembly 13 as desired. As such, circuit board assembly 91 includes a microprocessor 103 coupled with a circuit board 105. A pair of receiving terminals 107 are disposed on the circuit board 105 proximate a bracket 106, configured to receive electrodes 61 extending from the battery 26 and electronically couple the battery 26 to the circuit board 105 to energize the circuit board assembly 91. Similarly, a pair of receiving terminals 109 are disposed on the circuit board 105, configured to receive electrodes 71 extending from oven assembly 13 and electronically couple the oven assembly 13 with the circuit board assembly 91. Circuit board assembly 91 further includes an identification terminal 111 and an identification terminal 113, whereby identification terminal 111 is configured to receive first identification prong 85 therein and identification terminal 113 is configured to receive second identification prong 87 therein. As such, circuit board assembly 91 may poll identification terminal 111 and identification terminal 113 to determine whether the particular selected oven assembly 13 includes one or both of the first identification prong 85 and the second identification prong 87, or whether the selected oven assembly 13 does not include either prong. As discussed above, the circuit board assembly 91 can derive the particular heating profile for the selected oven assembly 13 based on the presence or absence of one or both of the first identification prong 85 and the second identification prong 87.

Circuit board assembly 91 further includes a temperature sensor 115 extending from circuit board 105 and oriented to be proximate the oven assembly 13 when an oven assembly 13 is disposed in heater receptacle 95. Temperature sensor 115 is illustrative of one embodiment of the present invention, as circuit board assembly 91 may further include multiple infrared sensors (not shown), thermocouple style sensors (not shown), and thermistors style sensors (not shown) for precise sensing or derivation of the temperature of the medium for use in control of the heat directed at the smoking substance or medium. Circuit board assembly 91 further includes a jumper socket 116 configured to receive corresponding electrical wiring (not shown) from display screen 19 and button 21 and electronically and logically couple display screen 19, button 21, and microprocessor 103 such that microprocessor 103 may actuate display screen 19 in accordance with the logic stored therein and in accordance with actuation of the button 21 by the user. While circuit board assembly 91 is shown as a feature of oven mount assembly 15, in other embodiments of the present invention, circuit board assembly 91 or a similar element thereof, may be disposed in other assemblies or components of PEV 1. For example, in an embodiment of the invention, a circuit board assembly may be disposed in the top shell assembly 9. Alternatively, PEV 1 may include a master controller and slave controller disposed anywhere in the PEV 1 and in communication through various wiring and logic circuitry.

Backing plate 93 is sized and configured to brace circuit board assembly 91 and hold circuit board assembly 91 firmly between cap 89 and backing plate 93. As such, backing plate 93 includes a plurality of fastener receivers 117 for receiving a corresponding series of fasteners 119 therein, whereby fasteners 119 are configured to pin and hold the circuit board assembly 91 to backing plate 93. Backing plate 93 defines a pair of apertures 121 aligned and sized to allow electrodes 61 from battery 26 to pass through backing plate 93 and into receiving terminals 107 of circuit board assembly 91.

Figure 12:
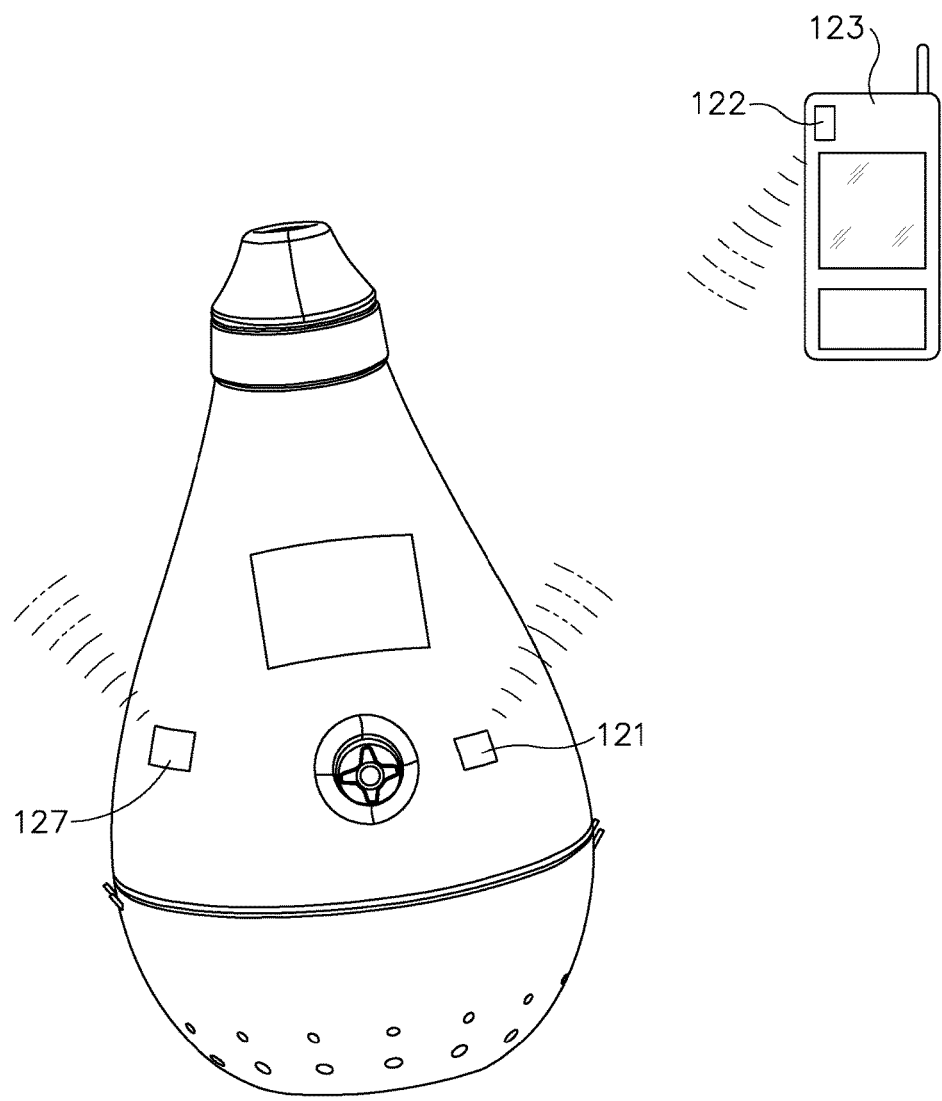
FIG. 12 is a perspective view of the personal electronic vaporizer of FIG. 1 and a mobile communication device.

As shown in FIG. 12, PEV 1 may include a wireless module 121 electronically coupled with microprocessor 103 through corresponding wiring (not shown). Wireless module 121 is configured to wirelessly electronically couple with a corresponding wireless communication module 122 of a mobile communication device 123. The mobile communication device 122 includes logic and circuitry to connect wireless communication module 122 with an interface application 125 having a graphical user interface (not shown). The interface application 125 may be configured to respond to input from the user and transmit these user commands from mobile communication device 1 to PEV 1. In turn, PEV 1 is configured to receive these user commands via the wireless module 121 and provide these commands to microprocessor 103. Microprocessor 103 interprets these user commands and actuates the various components and elements of PEV 1 accordingly. Microprocessor 103 is further configured to collect various metrics, data points, and related information and provide this data to mobile communication device 123 for display to the user through interface application 125.

PEV 1 may further include a speaker 127 electronically coupled with microprocessor 103 through corresponding wiring (not shown). Speaker 127 is configured to receive information and data from microprocessor 103 and transmit sound waves in accordance with the received information. For example, microprocessor 103 may provide musical data to speaker 127, whereby speaker 127 transmits this musical data as sound waves to the user through PEV 1. Speaker 127 may ultimately be controlled by a user through any combination of display screen 19, button 21, and interface application 125 on mobile communication device 123.

Figure 13:
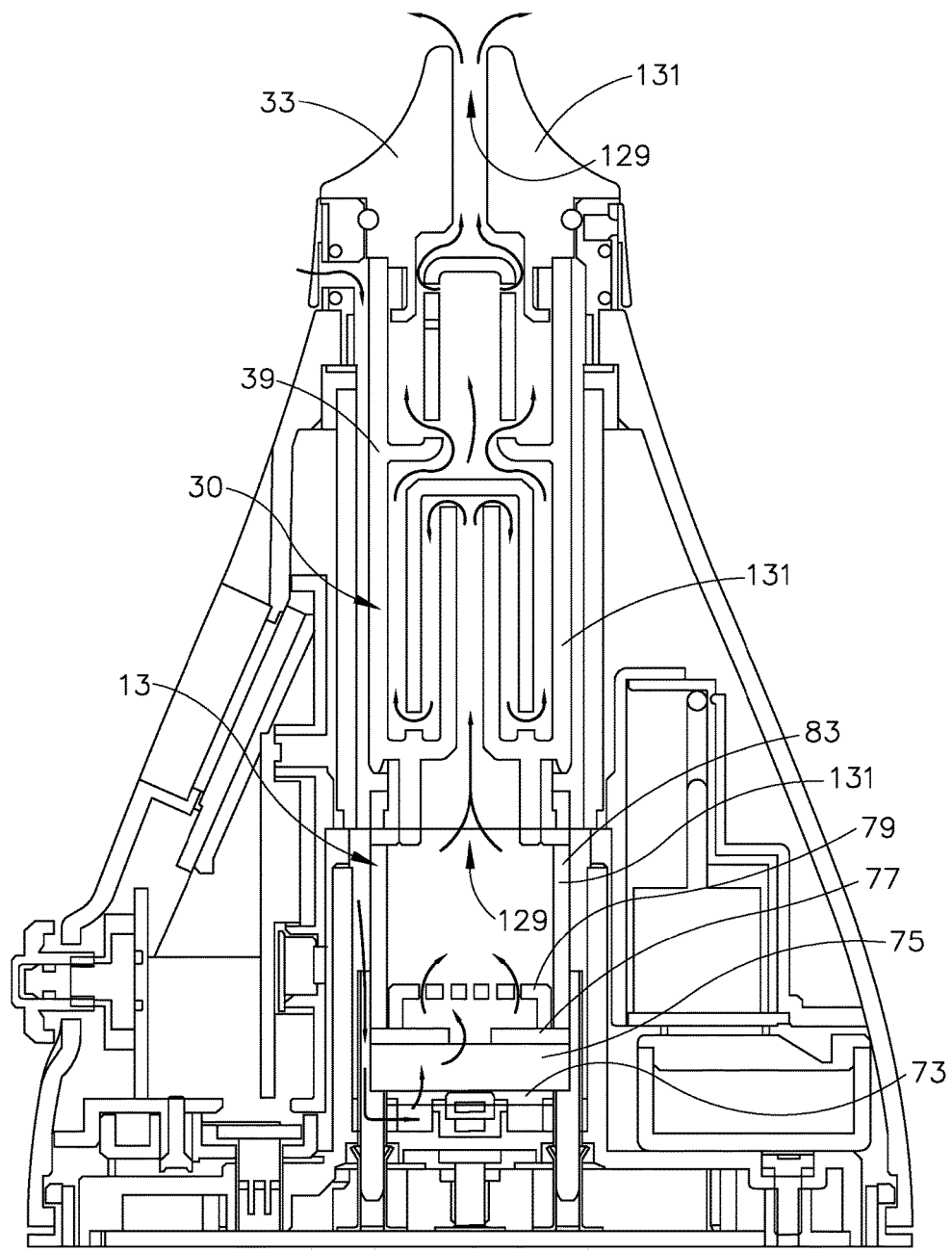
FIG. 13 is an enlarged view of a portion of FIG. 3.

PEV 1 may further include a pathway 129 surrounded entirely by a material 131 and extending from inside the oven assembly 13 out through the mouthpiece channel 29 of the mouthpiece assembly 7. As shown in FIG. 13 and starting inside the oven assembly 13, tray 75, ring 77, oven base 79, and cylindrical shroud 83 are all formed of the material 131. Further, shaft 34 defining bubbler area 30 and mouth area 33 are also formed of the material 131. As such, as the medium is heated in oven assembly 13, the medium itself and the vapors emitted therefrom is entirely surrounded by the material 131 as the vapors travel along pathway 129. In an embodiment of the invention, the material is inert, chemically stable, and thermodynamically stable. This ensures the vapors are untainted by the material as the vapors travel along pathway 129. Further, by heating oven assembly 13 through heating plate 73, situated outside of pathway 129, the vapors are untainted by electrical components of PEV 1, such as heating coils or other undesirable elements that may alter the vapors or the medium in undesirable ways. In an embodiment of the invention, the material 131 is a relatively pure glass material, a ceramic glass material, a relatively pure ceramic material, or a polycarbonate material. The term "relatively pure" signifies the material may include some common slight impurities or colorants.

In operation, a user my grasp PEV 1 and rotate top shell assembly 9 and battery compartment assembly 17 axially to disengage latch 63 and release the two components. This release exposes container assembly 11 to the user, which may be detached from around heater receptacle 95 of oven mount assembly 15. The user thereafter opens lid 53 of compartment assembly 17 to expose the medium stored in hollow body 51. Depending on the medium, the user thereafter selects the appropriate oven assembly 13. For example, if the medium is a solid, the user may select a corresponding oven assembly 13 configured to properly and efficiently heat a solid medium using a particular heating profile associated with the selected oven assembly 13. Alternatively, if the medium is a liquid or a wax, another more appropriate oven assembly 13 may be selected.

Figure 4:
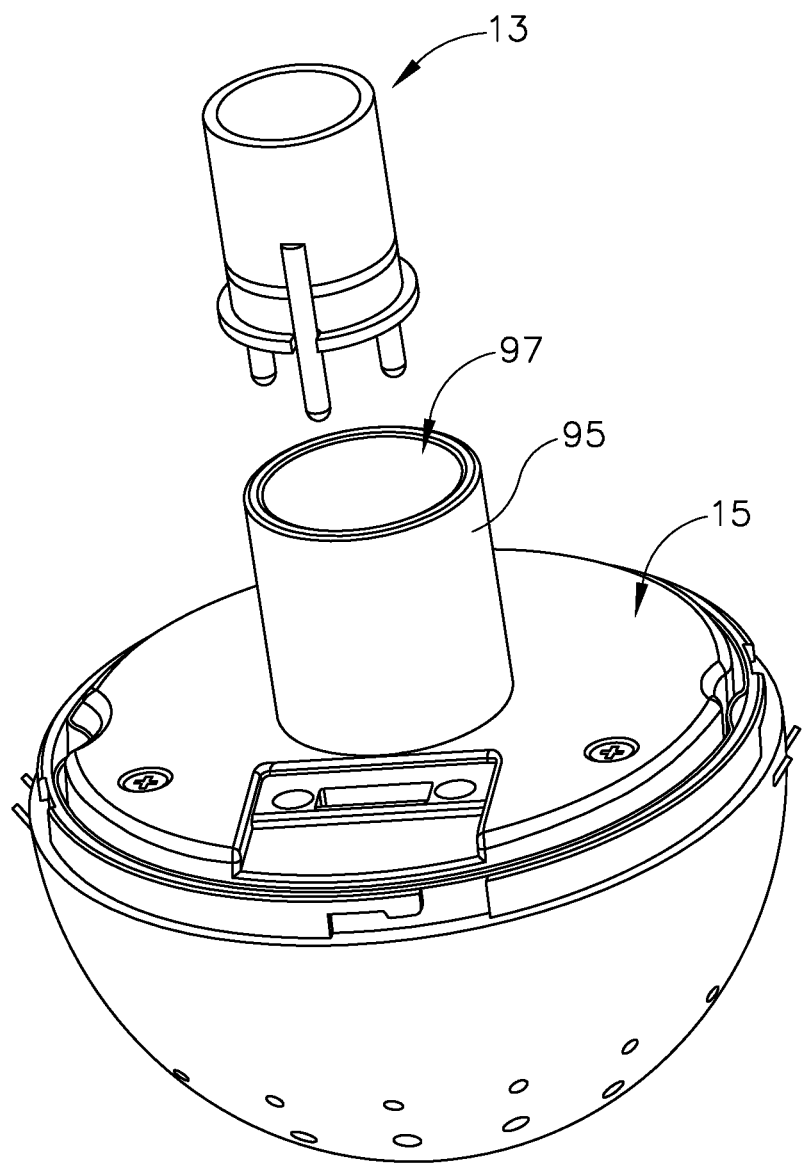
FIG. 4 is a perspective view of an embodiment of an oven assembly, an embodiment of an oven mount assembly, and an embodiment of a battery compartment assembly of the present invention.

After the oven assembly 13 is selected, the user inserts the medium into the cylindrical shroud such that the medium rests on oven base 79. As illustrated in FIG. 4, the user thereafter inserts the selected oven assembly 13 into channel 97 of heater receptacle 95 of oven mount assembly 15 in the direction of Arrow D. The oven assembly 13 is inserted into heater receptacle 95 in a particular orientation, whereby each electrode 71A and 71B is passed through electrode through holes 99 of cap 89 and is received in corresponding receiving terminals 109 of circuit board assembly 91. Similarly, if the selected oven assembly 13 includes a first identification prong 85, the first identification prong 85 is passed through one of the identification prong through holes 101 and is received in corresponding receiving terminal 111 of circuit board assembly 91. If the selected oven assembly 13 includes second identification prong 87, the second identification prong 87 is passed through one of the identification prong through holes 101 and is received in corresponding receiving terminal 113 of circuit board assembly 91.

Once the selected oven assembly 13 is loaded with the medium and inserted into the oven mount assembly 15, the user then aligns top shell assembly 9 with battery compartment assembly 17 and axially twists the two elements to engage latch 63 to firmly hold top shell assembly 9 to battery compartment assembly 17. If desired, the user may then remove the mouthpiece assembly 7 and fill bubbler area 30 with liquid, such as water, for filtering the vapors of the medium.

Once the mouthpiece assembly 7 is coupled with the top shell assembly 9 and the selected oven assembly 13 is disposed in the oven mount assembly 15, the PEV 1 is actuated to heat the medium in the oven assembly 13. The heating may be actuated by the user through manual manipulation of button 21 or through manipulation of interface application 125 on mobile communication device 123 and feedback may be provided to the user through display screen 19.

In response to a heating request by the user, the microprocessor 103 polls identification terminal 111 and identification terminal 113 to determine the particular configuration, through a combination of the presence or absence of the first identification prong 85 and the second identification prong 87, of the selected oven assembly 13. In one example, the presence or absence of the identification prongs correlates to a two digit binary number such as 00, 01, 10, or 11 stored in a lookup table in the microprocessor 103. The microprocessor 103 thereafter retrieves the particular heating profile associated with the configuration of the identification prongs and initiates heating of the heating plate 73 in accordance with the retrieved heating profile. The heating of heating plate 73 is performed by energizing heating plate 73 through a current supplied by battery 26 and tailored to the heating profile.

Next, the medium is heated in the oven assembly 13 through heating of the heating plate 73. The user thereafter orally engages mouth area 33 of mouthpiece assembly 7 and applies negative pressure on the mouthpiece assembly 7 to draw air through PEV 1. The negative pressure at mouthpiece assembly 7 draws air from primary intake opening 35 and secondary intake openings 37 through oven assembly 13 and around the heated medium. The vapors from the heated medium are drawn up through pathway 129, through bubbler area 30, and into mouthpiece channel 29, where the vapors are inhaled or otherwise utilized by the user. The user may selectively rotate ring 31 on top shell assembly 9 to expose or cover primary intake opening 35 and/or secondary intake openings 37 and customize the pressure and air flow through the PEV 1. The vapors from the heated medium travel along pathway 129, which is entirely surrounded by material 131 configured to not taint or chemically disrupt the vapors.

The entire experience may be enhanced by actuating PEV 1 to play music or other audible sounds through speaker 127.

Figure 15:
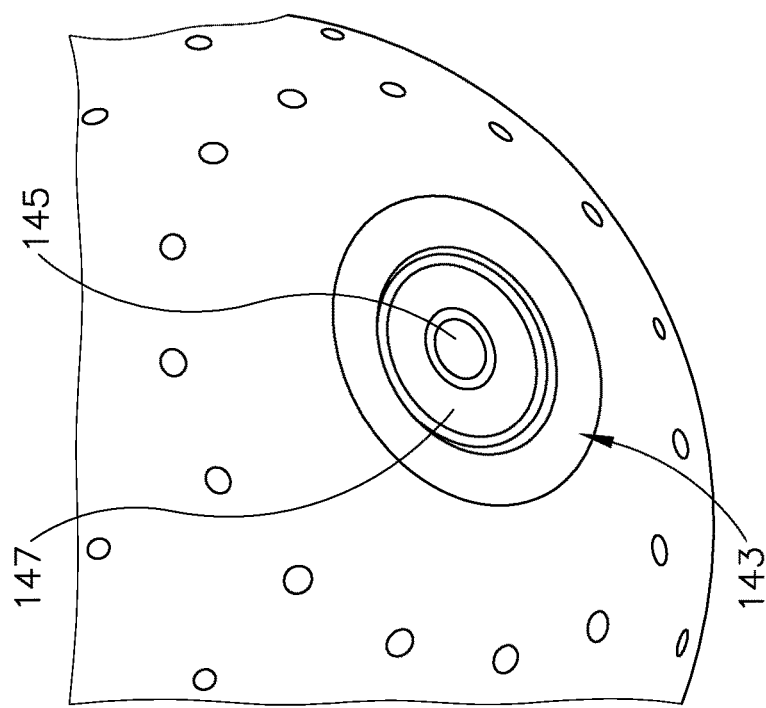
FIG. 15 is a perspective view of the lower surface of battery compartment assembly of the present invention.
Figure 14:
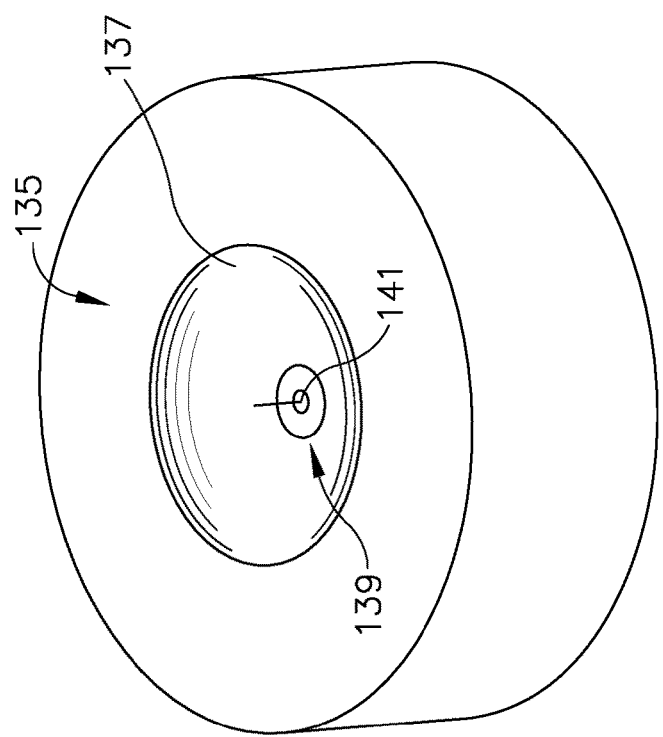
FIG. 14 is a perspective view of an embodiment of a charging base of the present invention.

As shown in FIGS. 14 and 15, a charging base 135 may be provided to recharge battery 26. Charging base 135 includes a power cord (not shown) configured to draw power from a wall outlet or other similar power source. Charging base 135 further includes a recess 137, wherein a positive charging pole 139 and a negative charging pole 141 reside. As shown on FIG. 15, the bottom surface of battery compartment assembly 17 may include a charging area 143 complementarily shaped to mate with recess 137. Charging area 143 includes a positive charging pole 147 configured to mate with positive charging pole 139 and a negative charging pole 145 configured to mate with negative charging pole 141. The mating of the poles completes a charging circuit between battery 26 and charging base 135 and acts to recharge battery 26. Charging base 135 may be configured to provide over five amps of charging to the battery 26. In one embodiment of the charging base 135, the battery 26 is charged using a twenty amp circuit to allow for quick charging of battery 26, which may be less than ten minutes. While charging base 135 is shown and described herein, any other mechanism for recharging battery 26 is contemplated, such as a USB style power cord or a standard power cord plugged directly into the body of battery compartment assembly 17.

We claim:

1. A device comprising:
    a mouthpiece assembly defining a mouthpiece channel and including an external portion and an internal portion;
    a shell assembly extending between a first end and a second end and defining a shell pocket therein, wherein the shell pocket opens through the first end and is configured to slidably receive the internal portion of the mouthpiece assembly therein;
    a first oven assembly including a heating chamber surrounded by a material;
    a second oven assembly including a heating chamber surrounded by the material;
    a battery compartment assembly removably secured to the second end of the shell assembly; and
    an oven mount assembly secured to the battery compartment assembly, wherein the oven mount assembly is configured to selectively receive one of the first oven assembly and the second oven assembly and align the heating chamber of the selected oven assembly with the mouthpiece channel when the battery compartment is secured to the second end of the shell assembly, wherein the oven mount assembly is configured to receive the first oven assembly in a first orientation and thereby electronically couple the first oven assembly to the battery in accordance with a first heating profile, wherein the oven mount assembly is configured to receive the second oven assembly in a second orientation and thereby electronically couple the second oven assembly to the battery in accordance with a second heating profile.

2. The device of claim 1, wherein the material is glass.

3. The device of claim 1, wherein the first oven assembly further includes a heating coil operable to heat the first oven assembly in accordance with the first heating profile, and wherein the second oven assembly further includes a heating coil operable to heat the second oven assembly in accordance with a second heating profile.

4. The device of claim 3, wherein the oven assembly includes an electrode extending from the heating plate, wherein the oven mount assembly defines a through hole for selectively engaging the electrode when the oven assembly is disposed in the heater receptacle.

5. The device of claim 1, wherein the first oven assembly further includes a first heating plate and wherein the second oven assembly further includes a second heating plate.

6. The device of claim 5, wherein the first heating plate is operable to heat the first oven assembly in accordance with the first heating profile, and wherein the second heating plate is operable to heat the second oven assembly in accordance with the second heating profile.

7. The device of claim 1 wherein the first end of the shell assembly includes a first diameter and a second end having a second diameter, and wherein the first diameter is smaller than the second diameter.

8. The device of claim 1, wherein the first oven assembly further includes a first plug and a second plug, and wherein the second oven assembly further includes a third plug and a fourth plug.

9. The device of claim 8, wherein the oven mount assembly includes a first socket, a second socket, and a third socket, wherein the first socket is configured to receive the first plug and the second socket is configured to receive the second plug when the selected oven is the first oven assembly, and wherein the third socket is configured to receive the third plug and the first socket is configured to receive the fourth plug when the selected oven is the second oven assembly.

10. The device of claim 1, further comprising:
    an opening defined by the external portion of the mouthpiece; and
    a pathway extending from the opening through the mouthpiece to the heating chamber of the first oven assembly when the first oven assembly is disposed in the oven mount.

11. The device of claim 10, wherein the pathway is surrounded by glass.

12. The device of claim 1, further comprising a wireless communication module disposed in one of the shell assembly, the oven mount assembly, and the battery compartment assembly, wherein the wireless communication module is configured to receive a set of instructions wirelessly and actuate the battery.

13. The device of claim 1, further comprising:
    a speaker disposed in one of the shell assembly, the oven mount assembly, and the battery compartment assembly; and
    a wireless communication module disposed in one of the shell assembly, the oven mount assembly, and the battery compartment assembly, wherein the wireless communication module is configured to receive a set of instructions wirelessly and actuate the speaker.

14. A device comprising:
    a mouthpiece assembly defining a mouthpiece channel and including an external portion and an internal portion;
    a shell assembly extending between a first end and a second end and defining a shell pocket therein, wherein the shell pocket opens through the first end and configured to slidably receive the internal portion of the mouthpiece assembly therein;
    a first oven assembly including a heating chamber surrounded by a material and a first identification prong;
    a second oven assembly including a heating chamber surrounded by the material and a second identification prong;
    a battery compartment assembly removably secured to the second end of the shell assembly; and
    an oven mount assembly secured to the battery compartment assembly, wherein the oven mount assembly is configured to selectively receive one of the first oven assembly and the second oven assembly and align the heating chamber of the selected oven assembly with the mouthpiece channel when the battery compartment is secured to the second end of the shell assembly, wherein the oven mount assembly is configured to receive the first identification prong and thereby electronically couple the first oven assembly to the battery in accordance with a first heating profile, wherein the oven mount assembly is configured to receive the second identification prong and thereby electronically couple the second oven assembly to the battery in accordance with a second heating profile.

15. The device of claim 14, wherein the first heating profile includes a first goal temperature range, and wherein the second heating profile includes a second goal temperature range.

16. The device of claim 15, further comprising:
a sensor;
a microprocessor electronically coupled with the battery and the sensor, wherein the microprocessor is configured to heat a first medium disposed in the first oven assembly into the first goal temperature range, and wherein the microprocessor is configured to heat a second medium disposed in the second oven assembly into the second goal temperature range.

17. The device of claim 16, further comprising a preheating chamber defined by the oven mount assembly, wherein the preheating chamber is oriented and configured to preheat air before the air enters the oven assembly.

18. The device of claim 17, further comprising:
a shell aperture defined by the shell assembly; and
a ring having a ring aperture defined therein and rotatable about a portion of the shell assembly, wherein the ring is configured to selectively rotate to open and close fluid communication between the ring aperture and the shell aperture.

19. The device of claim 14, further comprising a third oven assembly including a heating chamber surrounded by the material and a third identification prong, wherein the oven mount assembly is configured to selectively receive the third oven assembly and align the heating chamber of the third oven assembly with the mouthpiece channel, wherein the oven mount assembly is configured to receive the third identification prong and thereby electronically couple the third oven assembly to the battery in accordance with a third heating profile.

20. The device of claim 14, further comprising at least one infra-red sensor disposed in one or more of the mouthpiece assembly, first oven assembly, second oven assembly, oven mount assembly, and battery compartment assembly, wherein the infra-red sensor is configured to sense a temperature of the device, and wherein the device is configured to use the sensed temperature to optimize temperature control of the device.

* * * * *